(12) United States Patent
Kajihara et al.

(10) Patent No.: US 9,944,732 B2
(45) Date of Patent: Apr. 17, 2018

(54) RADICAL POLYMERIZATION INITIATOR, MULTI-BRANCHED POLYMER, VARNISH, ADHESIVE AGENT, COATING MATERIAL, SEALING MATERIAL, SEMICONDUCTOR, AND ELECTRONIC DEVICE

(71) Applicant: Hitachi, Ltd., Chiyoda-ku, Tokyo (JP)

(72) Inventors: Yuri Kajihara, Tokyo (JP); Takahito Muraki, Tokyo (JP); Jun Nunoshige, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/105,034

(22) PCT Filed: Dec. 27, 2013

(86) PCT No.: PCT/JP2013/085029
§ 371 (c)(1),
(2) Date: Jun. 16, 2016

(87) PCT Pub. No.: WO2015/097835
PCT Pub. Date: Jul. 2, 2015

(65) Prior Publication Data
US 2016/0319056 A1 Nov. 3, 2016

(51) Int. Cl.
| | | |
|---|---|---|
| *C08F 120/14* | (2006.01) | |
| *C07F 5/02* | (2006.01) | |
| *C08F 112/08* | (2006.01) | |
| *C09J 125/06* | (2006.01) | |
| *C09J 133/12* | (2006.01) | |
| *C08F 12/08* | (2006.01) | |
| *C08F 4/52* | (2006.01) | |
| *C08F 4/04* | (2006.01) | |
| *C09D 125/06* | (2006.01) | |
| *C09D 133/12* | (2006.01) | |

(52) U.S. Cl.
CPC ............ *C08F 120/14* (2013.01); *C07F 5/025* (2013.01); *C08F 4/04* (2013.01); *C08F 4/52* (2013.01); *C08F 12/08* (2013.01); *C08F 112/08* (2013.01); *C09D 125/06* (2013.01); *C09D 133/12* (2013.01); *C09J 125/06* (2013.01); *C09J 133/12* (2013.01); *H01L 2224/48247* (2013.01); *H01L 2924/181* (2013.01)

(58) Field of Classification Search
CPC .... C08F 120/14; C08F 112/08; C09D 125/06; C09D 133/12; C09J 125/06; C09J 133/12
See application file for complete search history.

(56) References Cited

U.S. PATENT DOCUMENTS

| | | | |
|---|---|---|---|
| 2,985,633 A | 5/1961 | Welch | |
| 4,676,858 A | 6/1987 | Ritter | |
| 2005/0027086 A1 | 2/2005 | Kennedy et al. | |
| 2006/0191623 A1* | 8/2006 | Lutz | B29C 65/485 |
| | | | 156/94 |

FOREIGN PATENT DOCUMENTS

| | | | | |
|---|---|---|---|---|
| JP | 58-84803 A | 5/1983 | | |
| JP | 9-511784 A | 11/1997 | | |
| JP | 2003-252919 A | 9/2003 | | |
| JP | 2005-281453 A | 10/2005 | | |
| JP | 2006-523767 A | 10/2006 | | |
| JP | 2010-506002 A | 2/2010 | | |
| JP | 2003-252919 | * | 9/2013 | ............... C08F 4/12 |
| WO | WO 96/23012 A1 | 8/1996 | | |
| WO | WO 2008/045372 A2 | 4/2008 | | |

OTHER PUBLICATIONS

International Search Report (PCT/ISA/210) issued in PCT Application No. PCT/JP2013/085029 dated Apr. 8, 2014 with English translation (7 pages).
Japanese-language Written Opinion (PCT/ISA/237) issued in PCT Application No. PCT/JP2013/085029 dated Apr. 8, 2014 (5 pages).
Kanno, "Tokushu na Radical Jugo Kaishizai to shite no Pinacolborane ni Kansuru Kenkyu", Abstracts, Annual Meeting of the Society of Polymer Science, Japan, 2007, vol. 56, No. 1, 1Pb002 (3 pages).

* cited by examiner

*Primary Examiner* — Robert Harlan
(74) *Attorney, Agent, or Firm* — Crowell & Moring LLP

(57) ABSTRACT

This invention is intended to synthesize a multi-branched polymer, which has an uniform molecular chain lengths and is free from branch defects, without the need for purification. This invention is also intended to synthesize a polyfunctional radical polymerization initiator represented by Formula 1:

Formula 1

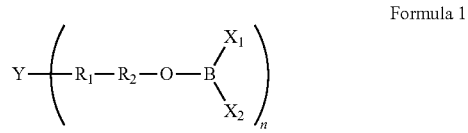

wherein n is an integer of 1 or larger; Y is a polyfunctional unsaturated compound; $R_1$ is a hydrocarbon group; $R_2$ is a structure in which one molecule of a radically polymerizable unsaturated hydrocarbon compound is bound to $R_1$ and the oxygen atom; $X_1$ of B—$X_1$ (boron-$X_1$) bond is an alkoxy or phenyl group; and $X_2$ of B—$X_2$ (boron-$X_2$) bond is an alkoxy or phenyl group.

12 Claims, 1 Drawing Sheet

RADICAL POLYMERIZATION INITIATOR, MULTI-BRANCHED POLYMER, VARNISH, ADHESIVE AGENT, COATING MATERIAL, SEALING MATERIAL, SEMICONDUCTOR, AND ELECTRONIC DEVICE

TECHNICAL FIELD

The present invention relates to a radical polymerization initiator and a multi-branched polymer.

BACKGROUND ART

In recent years, multi-branched polymers (star-shaped polymers) have drawn attention because of distinctive properties thereof, such as low viscosity, particulate properties, and molecular functions. Accordingly, various techniques for synthesis of such polymers have been known. The technique for synthesis disclosed in JP 2010-506002 A (Patent Document 1) involves the use of, as a catalyst, a lanthanoid compound, a nickel-containing compound, or an organic metal compound. Thus, a process of purification thereof is necessary. JP 2003-252919 A (Patent Document 2) describes a polyfunctional radical polymerization initiator, which is preferably used for the production of a multi-branched polymer, composed of a compound comprising 3 or more ethylenic double bonds in a single molecule and a boron compound added to the double bonds (see the abstract).

CITATION LIST

Patent Documents

Patent Document 1: JP 2010-506002 A
Patent Document 2: JP 2003-252919 A

SUMMARY OF THE INVENTION

Object to be Attained by the Invention

The present invention is intended to synthesize a multi-branched polymer, which has an uniform molecular chain length and is free from branch defects, without the need for purification.

Means for Attaining the Object

The present invention includes a plurality of means in order to attain the above object. An example is a polyfunctional radical polymerization initiator represented by a formula, wherein n is an integer of 3 or larger and X in B—X bond is an alkoxy or phenyl group.

Effects of the Invention

According to the present invention, a multi-branched polymer, which has an uniform molecular chain length and is free from branch defects or unnecessary molecular chains, can be synthesized, without the need for purification.

EMBODIMENTS FOR CARRYING OUT THE INVENTION

Figure 1:
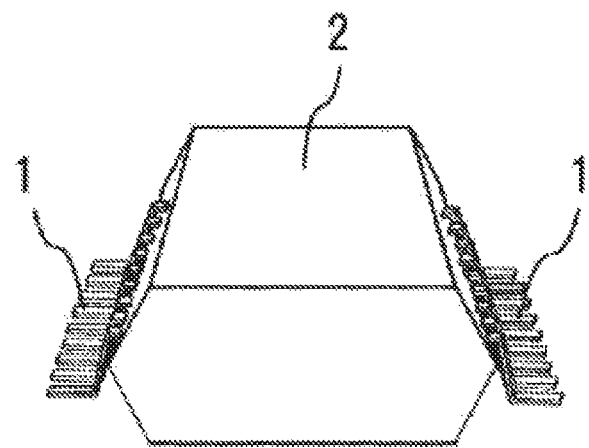
FIG. 1 is a perspective view showing an appearance of a package using the multi-branched polymer according to the present invention for mold sealing.

Hereafter, the embodiments of the present invention are described with reference to the drawings.

The present invention relates to a method of living radical polymerization involving the use of a boron compound, a radical polymerization initiator exhibiting living radical polymerizability, and a multi-branched polymer synthesized with the use of such polymerization initiator.

The polyfunctional radical polymerization initiator of the present invention is represented by Formula 1, wherein n is an integer of 3 or larger, and $X_1$ and $X_2$ of B—$X_1$ and B—$X_2$ bonds each represent an alkoxy or phenyl group.

$$Y \left( R_1 - R_2 - O - B \begin{matrix} X_1 \\ X_2 \end{matrix} \right)_n \quad \text{Formula 1}$$

In the formula representing the polyfunctional radical polymerization initiator, $X_1$ and $X_2$ may not necessarily be the same functional group, but they may be different functional groups.

In the formula representing the polyfunctional radical polymerization initiator according to the present invention, $R_1$ is a hydrocarbon group, and $R_2$ is a structure in which one molecule of a radically polymerizable unsaturated hydrocarbon compound is bound to $R_1$ and the oxygen atom.

A specific structure represented by $R_2$ is exemplified in the form of an unsaturated hydrocarbon compound before it is positioned between $R_1$ and the oxygen atom. Such unsaturated hydrocarbon compound is selected from the group consisting of an aromatic vinyl compound, an aromatic allyl compound, a heterocycle-containing vinyl compound, a heterocycle-containing allyl compound, alkyl (meth)acrylate, unsaturated monocarboxylic acid ester, fluoroalkyl (meth)acrylate, a siloxanyl compound, a mono-(meth)acrylate and di-(meth)acrylate of an alkylene glycol, an alkoxyalkyl (meth)acrylate, a cyanoalkyl (meth)acrylate, acrylonitrile, methacrylonitrile, an oligo(meth)acrylate of a polyhydric alcohol, hydroxyalkyl (meth)acrylate, a hydroxyalkylester of an unsaturated carboxylic acid, an unsaturated alcohol, an unsaturated (mono)carboxylic acid, an unsaturated polycarboxylic acid, an unsaturated polycarboxylic anhydrate, a monoester and diester of an unsaturated polycarboxylic acid or unsaturated polycarboxylic anhydrate, an epoxy-group-containing unsaturated compound, a diene compound, vinyl chloride, vinyl acetate, sodium isoprene sulfonate, a cinnamic acid ester, a crotonic acid ester, dicyclopentadienyl, and ethylidene norbornene.

Specific examples of particularly preferable unsaturated hydrocarbon compounds include styrene monomers and acrylic vinyl monomers, such as acrylic acid esters having polar substituents, such as carbonyl group and nitrile group, an acrylamide derivative, and acrylonitrile.

In the formula representing the polyfunctional radical polymerization initiator according to the present invention, Y has a branched or cyclic molecular structure and comprises at least one of hydrocarbon, nitrogen, silicon, and phosphorus.

In the formula representing the polyfunctional radical polymerization initiator, Y is a compound having a molecular structure selected from the group consisting of ester bond, urethane bond, amide bond, thioester bond, siloxane bond, carbonyl group, carboxyl group, amino group, alkylamino group, dialkylamino group, pyridyl group, pyrrolidyl group, isocyanuric acid ester skeleton, cyanuric acid ester skeleton, hexahydrotriazine skeleton, maleimide skeleton, imidazole skeleton, and organic silicon skeleton.

In the formula representing the polyfunctional radical polymerization initiator according to the present invention, $R_1$—$R_2$ bond is an alkyl bond.

Hereafter, two ways of methods for synthesizing the polyfunctional radical polymerization initiator according to the present invention are described, although methods of synthesis are not limited thereto.

<Method of Synthesis 1>

A compound represented by Formula 2 is a precursor compound of the polyfunctional radical polymerization initiator according to the present invention.

In Formula 2, n is an integer of 1 or larger, and $X_1$ and $X_2$ of B—$X_1$ and B—$X_2$ bonds each represent an alkoxy or phenyl group.

Formula 2 represents a compound resulting from the addition of a boron compound to a polyfunctional unsaturated compound in which the boron compound comprises an alkoxy or phenyl group.

Examples of boron compounds include, but are not limited to, 4,4,5,5-tetramethyl-1,3,2-dioxaborolane (Pinacolborane) and diphenylborane. It is not necessary for $X_1$ and $X_2$ to be the same functional group, so they may be different functional groups.

A boron compound can be added to a polyfunctional unsaturated compound via hydroboration, although the addition reaction is not limited thereto.

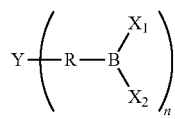

Formula 2

The polyfunctional unsaturated compound used in the present invention is not particularly limited, provided that it is an unsaturated monomer having an unsaturated bond and capable of performing an addition reaction with a borane compound (e.g., hydroboration).

The compound according to the present embodiment represented by Formula 2 can be obtained by radical polymerization of any known unsaturated monomer capable of hydroboration.

It is preferable that the polyfunctional unsaturated compound comprise one or more atoms selected from the group consisting of oxygen, nitrogen, phosphorus, sulfur, and halogen and have a linear, branched, or cyclic structure.

The polyfunctional unsaturated compound preferably has a structure having one atom as a center skeleton and at least two unsaturated hydrocarbon groups bound to the atom.

The polyfunctional unsaturated compound preferably has at least one type of molecular structure selected from the group consisting of ester bond, urethane bond, amide bond, thioester bond, siloxane bond, carbonyl group, carboxyl group, amino group, alkylamino group, dialkylamino group, and pyridyl group.

The polyfunctional unsaturated compound is preferably an organic silicon compound, an organic titanium compound, or an organic zirconium compound having a linear, branched, or cyclic molecular structure.

The polyfunctional unsaturated compound preferably has a molecular structure selected from the group consisting of pyrrolidyl group, isocyanuric acid ester skeleton, cyanuric acid ester skeleton, hexahydrotriazine skeleton, maleimide skeleton, imidazole skeleton, and organic silicon skeleton.

In the polyfunctional unsaturated compound, it is preferred that the molecular structure mentioned above is a cyclic molecular structure, and that the compound has the cyclic molecular structure as a center skeleton and at least two unsaturated bond groups in the side chain of the molecular structure.

The polyfunctional unsaturated compound preferably has a linear or branched molecular structure and comprises at least 2 unsaturated bond groups in the molecular structure.

The molecule of the polyfunctional unsaturated compound is preferably acrylamide, N,N-dimethyl acrylamide, 1-vinyl-2-pyrollidone, 2-vinyl pyridine, methacrylic acid, vinyltriethoxysilane, 3-methacryloxy propyltrimethoxysilane, p-styryltrimethoxysilane, tetraallylsilane, pentaerythritol tetraacrylate, divinyl benzene, diallyl isocyanurate, triallyl isocyanurate, triallyl cyanurate, trivinyl cyclohexane, trimethylolpropane triacrylate, dipentaerythritol tri(meth)acrylate, propionic acid-modified dipentaerythritol (meth)acrylate, pentaerythritol tri(meth)acrylate, propylene oxide-modified trimethylolpropane tri(meth)acrylate, isocyanuric acid-ethylene oxide-modified tri(meth)acrylate, pentaerythritol tetra(meth)acrylate, dipentaerythritol penta(meth)acrylate, propionic acid-modified dipentaerythritol penta(meth)acrylate, dipentaerythritol hexa(meth)acrylate, caprolactone-modified dipentaerythritol hexa(meth)acrylate, (meth)acrylate-modified polysiloxane or poly-1,2-butadiene.

The reaction between the polyfunctional unsaturated compound and the boron compound can be carried out in an adequate solvent with the use of the boron compound in an substantially stoichiometric amount relative to the amount of the polyfunctional unsaturated compound in the air or in an inert gas atmosphere, such as in a nitrogen gas atmosphere, at approximately 0° C. to 50° C. In such a case, examples of solvents include: aromatic hydrocarbons, such as benzene, toluene, and xylene; aliphatic or cycloaliphatic hydrocarbons, such as hexane, heptane, octane, and cyclohexane; esters, such as ethyl acetate and butyl acetate; ethers, such as dioxane and tetrahydrofuran and ketones, such as acetone, methyl ethyl ketone, and methyl isobutyl ketone. A single type of these solvents may be used alone or two or more type of solvents may be used in combination.

The resulting compound corresponds to a compound represented by Formula 2, which is a precursor of the polyfunctional radical polymerization initiator according to the present invention. A compound represented by Formula 2 may be used for polymerization of a radically polymerizable unsaturated compound without being isolated. Alternatively, a compound represented by Formula 2 may be isolated in accordance with a conventional technique and used for polymerization of a radically polymerizable unsaturated compound, according to need.

The polyfunctional radical polymerization initiator according to the present invention is a compound resulting from a reaction of one molecule of the radically polymerizable unsaturated hydrocarbon compound with the compound represented by Formula 2.

The polyfunctional radical polymerization initiator according to the present invention has functions as a dormant species in living radical polymerization.

The mechanisms for the reaction between the compound represented by Formula 2 and a radically polymerizable unsaturated hydrocarbon compound are as represented by Formulae 3, 4, and 5. In Formulae 3, 4, and 5, styrene is used as an example of an unsaturated hydrocarbon compound.

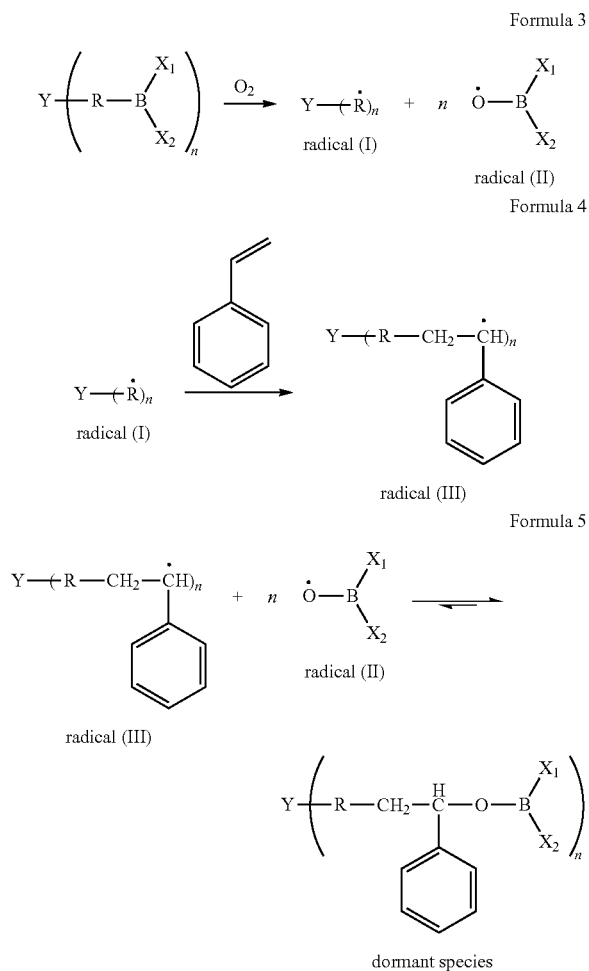

It is considered that a portion of the boron compound is cleaved by oxygen addition to form radical (I) and oxygen-centered radical (II) containing boron (Formula 3).

In the formula representing the polyfunctional radical polymerization initiator according to the present invention, B—X bond is stronger than B—R bond (i.e., a boron-alkyl bond). Accordingly, the oxidative cleavage always takes place at the site of B—R bond.

Since the oxidative cleavage always takes place at the site of B—R bond, undesirable branching does not occur, and the "n" branched chains grow equally during the growth reaction of the arms of the multi-branched polymer.

Radical (I) described above is highly active. Thus, it serves as a starting point of polymerization, and a radical polymerization of the radically polymerizable unsaturated hydrocarbon compound starts. Oxygen-centered radical (II) containing boron is added to the radical polymerization growth terminal (radical (III)) of an unsaturated hydrocarbon compound starting from radical (I), thereby forming the dormant species (Formula 5).

The resulting dormant species is the polyfunctional radical polymerization initiator according to the present invention.

<Method of Synthesis 2>

A reaction between an alcohol and boronic acid is relatively easy to occur, and boronic acid ester can be obtained via transesterification. The mechanisms of synthesis of the polyfunctional radical polymerization initiator according to the present invention through such reaction are shown in Formulae 6 and 7. $X_1$ and $X_2$ of B—$X_1$ and B—$X_2$ bonds each represent an alkoxy or phenyl group.

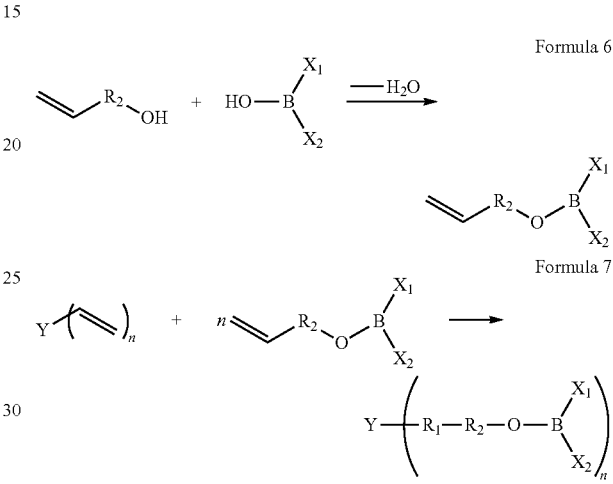

As shown in Formula 6, a compound having an alcoholic hydroxyl group is reacted with boronic acid having B—$X_1$ and B—$X_2$ bonds to generate boronic acid ester via transesterification. Subsequently, boronic acid ester is reacted with a polyfunctional unsaturated compound having an unsaturated bond by radical polymerization reaction to obtain the polyfunctional polymerization initiator according to the present invention.

It is preferable that the polyfunctional unsaturated compound comprise one or more atoms selected from the group consisting of oxygen, nitrogen, phosphorus, sulfur, and halogen and have a linear, branched, or cyclic structure.

The polyfunctional unsaturated compound preferably has a structure having one atom as a center skeleton and at least two unsaturated hydrocarbon groups bound to the atom.

The polyfunctional unsaturated compound preferably has at least one type of molecular structure selected from the group consisting of ester bond, urethane bond, amide bond, thioester bond, siloxane bond, carbonyl group, carboxyl group, amino group, alkylamino group, dialkylamino group, and pyridyl group.

The polyfunctional unsaturated compound is preferably an organic silicon compound, an organic titanium compound, or an organic zirconium compound having a linear, branched, or cyclic molecular structure.

The polyfunctional unsaturated compound preferably has a molecular structure selected from the group consisting of pyrrolidyl group, isocyanuric acid ester skeleton, cyanuric acid ester skeleton, hexahydrotriazine skeleton, maleimide skeleton, imidazole skeleton, and organic silicon skeleton.

The polyfunctional unsaturated compound preferably has a cyclic molecular structure as a center skeleton and at least two unsaturated bond groups in the side chain of the molecular structure.

The polyfunctional unsaturated compound preferably has a linear or branched molecular structure and comprises at least 2 unsaturated bond groups in the molecular structure.

The molecule of the polyfunctional unsaturated compound is preferably acrylamide, N,N-dimethyl acrylamide, 1-vinyl-2-pyrollidone, 2-vinyl pyridine, methacrylic acid, vinyltriethoxysilane, 3-methacryloxy propyltrimethoxysilane, p-styryltrimethoxysilane, tetraallylsilane, pentaerythritol tetraacrylate, divinyl benzene, diallyl isocyanurate, triallyl isocyanurate, triallyl cyanurate, trivinyl cyclohexane, trimethylolpropane triacrylate, dipentaerythritol tri(meth)acrylate, propionic acid-modified dipentaerythritol (meth)acylate, pentaerythritol tri(meth)acrylate, propylene oxide-modified trimethylolpropane tri(meth)acrylate, isocyanuric acid-ethylene oxide-modified tri(meth)acrylate, pentaerythritol tetra(meth)acrylate, dipentaerythritol penta(meth)acrylate, propionic acid-modified dipentaerythritol penta(meth)acrylate, dipentaerythritol hexa(meth)acrylate, caprolactone-modified dipentaerythritol hexa(meth)acrylate, (meth)acrylate-modified polysiloxane or poly-1,2-butadiene.

The polyfunctional polymerization initiator thus obtained has functions as a dormant species in living radical polymerization.

The polyfunctional radical polymerization initiator according to the present invention is considered to react with oxygen to generate a radically reactive species, as shown in the reaction formula represented by Formula 2.

A multi-branched polymer synthesized with the use of the polyfunctional radical polymerization initiator according to the present invention; i.e., a multi-branched polymer represented by Formula 1, will be explained below.

The polyfunctional radical polymerization initiator according to the present invention has functions as a dormant species in living radical polymerization. It has an equilibrated correlation with an active species (Radical IV) generated from the polyfunctional radical polymerization initiator as represented by Formula 8, and the equilibrium is shifted toward the polyfunctional radical polymerization initiator (the dormant species) side (Formula 8).

An unsaturated hydrocarbon compound is added only when radical IV is generated, and it is then reverted to the dormant species. Thus, living radical polymerization proceeds (Formulae 9 and 10).

Since the polyfunctional radical polymerization initiator according to the present invention has n starting points of polymerization (n is an integer of 1 or larger), n polymer chains grows as a result of living radical polymerization to obtain a multi-branched polymer having n uniform chain lengths.

Formula 8

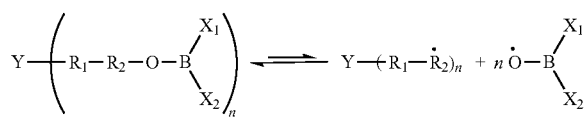

Formula 9

Formula 10

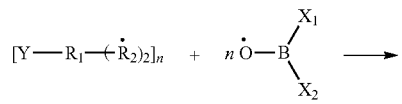

-continued

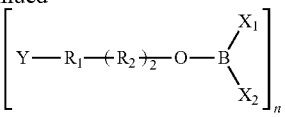

The use of the polyfunctional radical polymerization initiator according to the present invention enables synthesis of the multi-branched polymer according to the present invention, which has an uniform molecular chain length and is free from branch defects, without the need for purification of metal catalysts or the like.

The multi-branched polymer according to the present invention can be represented by Formula 11 below, wherein n is an integer of 1 or larger; and $R_{2m}$ represents a polymer of an unsaturated hydrocarbon compound. When n is an integer of 3 or larger, the multi-branched polymer is a star-shaped polymer.

Formula 11

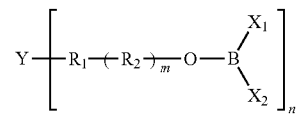

In the formula representing the multi-branched polymer according to the present invention, an unsaturated hydrocarbon compound represented by $R_{2m}$ is at least one unsaturated monomer selected from the group consisting of an aromatic vinyl compound, an aromatic allyl compound, a heterocycle-containing vinyl compound, a heterocycle-containing allyl compound, alkyl (meth)acrylate, unsaturated monocarboxylic acid ester, fluoroalkyl (meth)acrylate, a siloxanyl compound, mono(meth)acrylate and di(meth)acrylate of alkylene glycol, alkoxyalkyl (meth)acrylate, cyanoalkyl (meth)acrylate, acrylonitrile, methacrylonitrile, oligo (meth)acrylate of polyhydric alcohol, hydroxyalkyl (meth)acrylate, hydroxyalkylester of unsaturated carboxylic acid, unsaturated alcohol, unsaturated (mono)carboxylic acid, unsaturated polycarboxylic acid, unsaturated polycarboxylic anhydrate, monoester and diester of unsaturated polycarboxylic acid or unsaturated polycarboxylic anhydrate, an epoxy-group-containing unsaturated compound, a diene compound, vinyl chloride, vinyl acetate, sodium isoprene sulfonate, cinnamic acid ester, crotonic acid ester, dicyclopentadienyl, and ethylidene norbornene.

Specific examples of particularly preferable unsaturated hydrocarbon compounds include styrene monomers and acrylic vinyl monomers, such as acrylic acid esters having polar substituents, such as a carbonyl group and a nitrile group, acrylamide derivative, and acrylonitrile.

As $R_{2m}$, the unsaturated hydrocarbon compounds mentioned above can be also used in combination. In such a case, the resulting multi-branched polymer would have copolymer arms.

Depending on the combination of unsaturated hydrocarbon compounds, the resulting multi-branched polymer would have amphipathic polymer chains, and such polymer would be capable of adsorption/desorption of particular substances.

Polymerization temperature is generally 0° C. to 100° C., and preferably 10° C. to 70° C. Polymerization may be carried out in the air or in inert gas atmosphere such as in a nitrogen gas atmosphere. Since an active boraoxy group is bound to the growth terminus, methanol or the like may be added to inactivate such group, or the boraoxy group may be substituted with a desired functional group. After the completion of the reaction, a polymer may be isolated in accordance with a conventional technique to obtain a multi-branched polymer.

The weight average molecular weight (Mw) of the multi-branched polymer obtained by a method of polymerization involving the use of the polyfunctional polymerization initiator according to the present invention is preferably 1,000 to 200,000, and more preferably 3,000 to 80,000. The molecular weight distribution (Mw/Mn) is preferably 1.0 to 5.0, and more preferably 1.0 to 2.5.

The multi-branched polymer can be dissolved in an organic solvent and used in the form of a varnish. An organic solvent contained in the varnish is a common organic solvent. Specific examples thereof include alcohol, ketone, and an aromatic compound. Specific examples of alcohols that can be used as solvents include 2-methoxyethanol, 2-ethoxyethanol, 2-propyloxyethanol, and 2-butoxyethanol. Specific examples of ketones include methyl ethyl ketone, isobutyl ethyl ketone, cyclohexanone, γ-butyrolactone, and N,N-dimethylformamide. Specific examples of aromatic compounds include toluene and xylene. A single type of solvent may be used alone, or two or more types of solvents may be used in any combination at any proportion.

Viscosity of the varnish comprising the multi-branched polymer is 100 to 100000 mPa·s, and preferably 600 to 4000 mPa·s.

The multi-branched polymer obtained by a method of polymerization involving the use of the polyfunctional polymerization initiator according to the present invention has a reduced volume compared with that of a high-molecular-weight compound having the same molecular weight. Thus, such multi-branched polymer exhibits lower solution viscosity and melt viscosity.

The multi-branched polymer has a larger molecular weight compared with a high-molecular-weight compound exhibiting the same solution viscosity and melt viscosity. Thus, improved strength can be expected.

Because of a spherical form inherent to the multi-branched polymer, the multi-branched polymer can have a high-density molecular structure, and impact resistance and heat resistance can also be expected.

The multi-branched polymer can be used for an adhesive agent and a coating material.

The multi-branched polymer can be used for a mold sealant, a potting material used for the manufacture of a mold sealant, a package for electronic part, and the like.

A mold sealant manufactured with the use of the multi-branched polymer according to the present invention has low viscosity. Accordingly, a microfabricated structure can be voidlessly made.

Specific examples thereof are described with reference to FIG. 1 and FIG. 2.

FIG. 1 is a perspective view of a dual inline package (DIP) 200 as a specific example of a package for electronic part in which the resin material according to this embodiment containing the multi-branched polymer represented by Formula 5 is applied as a mold sealant. FIG. 2 is a cross-sectional view of DIP 200 shown in FIG. 1.

Figure 2:
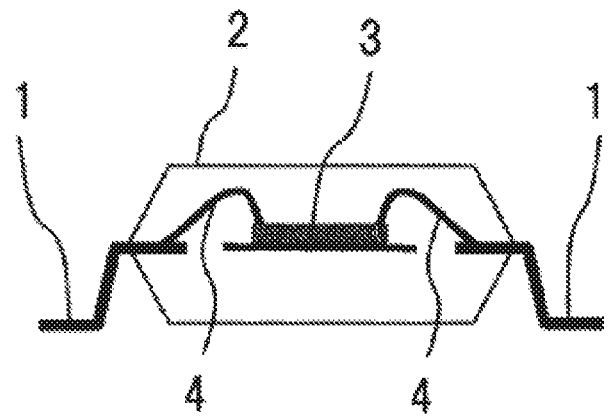
FIG. 2 is a cross-sectional view showing an internal structure of a package using the multi-branched polymer according to the present invention for mold sealing.

The DIP 200 shown in FIG. 1 and FIG. 2 includes semiconductor device 3 disposed on a substrate, lead frame 1 extending outward of mold sealant 2, and bonding wire 4 that electrically connects lead frame 1 and semiconductor device 3. A portion of read frame 1, semiconductor device 3, the substrate thereof, and bonding wire 4 are sealed by mold sealant 2 comprising the resin material according to this embodiment containing the multi-branched polymer represented by Formula 5.

Lead frame 1 and the bonding wire 4 each comprise a good conductor. Specifically, they comprises, for example, copper or aluminum. Further, the form of lead frame 1 and the bonding wire 4 can be in any known form, such as a solid wire or a twisted wire.

Semiconductor device 3 can have, for example, a circular shape, a divided circular shape, or a compressed shape. Further, the material for forming semiconductor device 3 is not particularly limited, provided that the material can be sealed by mold sealant 2.

Mold sealant 2 in the DIP 200 maintains resin strength and heat resistance substantially equal to those of conventional materials. Because of a high-density molecular structure of the multi-branched polymer, in addition, it has excellent heat resistance and impact resistance against, for example, fracture caused by impact to the circuit and abrupt thermal change accompanying heat generation of the circuit, compared with conventional chained resins, and improvement of reliability for the entire circuit can be expected. Further, there is an advantage that, upon repair treatment, a motion of the molecular chain is induced by the heat generated by current supply to the circuit, which can promote moderation and dispersion of the stress.

Hereafter, a method of mold sealing with the use of the resin material according to this embodiment (a mold sealing method) is described. Basically, this process is performed by forming the resin material in the same manner as in the method of manufacturing the resin material according to this embodiment described above. Specifically, the unsaturated monomer constituting the resin material according to this embodiment, the radical polymerization initiator, and, optionally, an organic solvent and the like are mixed, and semiconductor device 3 and the like are sealed with the use of the resulting mixture. Thus, semiconductor device 3 and the like can be sealed.

The mixture before polymerization can also be utilized as a potting material for mold sealing (that is, a potting material used for manufacturing the mold sealant). In general, the potting material is used by incorporating, for example, an inorganic filler and other resin materials, in addition to the components described above.

The potting material for manufacturing the mold sealant and the mold sealant are applicable, for example, to lead-frame type packages, such as System-on-Package (SOP) and Quad Flat Package (QFP); and a package for electronic parts, such as Ball Grid Array (BGA) and Multi-Chip Package (MCP), in addition to the DIP shown in FIG. 1. Further, the object to which the mold sealant is to be applied is not limited to the semiconductor part, but the sealant is also applicable to mold sealing of an electronic part having a size larger than that of the semiconductor part.

Hereafter, the present invention is described in greater detail with reference to the examples, although the technical scope of the present invention is not limited to these examples. In the examples, chemical shifts in the nuclear magnetic resonance spectra ($^1$H-NMR and $^{13}$C-NMR) were measured using FX270 (manufactured by JEOL Ltd.). A number average molecular weight and a weight average molecular weight of the polymer were determined by gel permeation chromatography (GPC).

For a polymer of a special structure having a plurality of polymerization initiation points, an absolute molecular weight was determined using a weight average molecular weight (Mw) determined by GPC and a multi-angle laser light scattering photometer (MALLS), He—Ne laser. DAWN DSP-F manufactured by Wyatt Co. under the same conditions.

Viscosity was measured using a rotational viscometer (HAAKE Viscotester 550) at 25° C.

The results of examples and comparative examples are summarized in Tables 1 and 2.

(Synthesis of Multi-branched Polymer Via Method of Synthesis 1)

EXAMPLE 1

<Trifunctional-pinacol-MMA>

Trifunctional acrylate (i.e., tris(2-acryloyloxyethyl)isocyanurate, 1 g, manufactured by Hitachi Chemical Company, Ltd.) was introduced into a two-necked, eggplant-type flask (hereafter, referred to as a "two-necked flask"), the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 7.4 ml of a solution of 4,4,5,5-tetrametramethyl-1,3,2-dioxaborolane (Pinacolborane) at the concentration of 1.0 mol/l in tetrahydrofuran (manufactured by Aldrich) was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

$^1$H-NMR: 5.2 ppm (CH2-B); $^{13}$C-NMR: 29 ppm (CH2-B)

A C—C double bond (C=C) observed in tris(2-acryloyloxyethyl)isocyanurate at 128 ppm in $^{13}$C-NMR and B—H bond (B—H) observed in 4,4,5,5-tetramethyl-1,3,2-dioxaborolane (Pinacolborane) at 4.8 ppm in $^1$H-NMR were not substantially observed. On the basis of these results, it was confirmed that a polymerization initiator in which 4,4,5,5-tetrametramethyl-1,3,2-dioxaborolane (Pinacolborane) had been added to a carbon-carbon double bond of tris(2-acryloyloxyethyl)isocyanurate was obtained. Thus, the precursor of the polyfunctional radical polymer of the present invention was obtained.

Subsequently, 0.71 g of methyl methacrylate as an unsaturated hydrocarbon compound was added to 0.5 g of the precursor in a two-necked flask using a syringe. Oxygen (5 ml) was injected thereinto using a gas-tight syringe at 23° C., so as to activate the polymerization initiator. Thus, the polyfunctional radical polymerization initiator according to the present invention serving as a dormant species was synthesized.

Thereafter, 18.6 g of methyl methacrylate was added using a syringe, polymerization was carried out in a nitrogen gas atmosphere at 60° C. for 5 hours, and a polymerization solution was subjected to reprecipitation using methanol (Wako Pure Chemical Co.). Thus, the polymer was obtained. The yield was 56.3%, the number average molecular weight of the polymer determined by GPC was 45,000, and the molecular weight distribution (i.e., weight average molecular weight/number average molecular weight (Mw/Mn)) was 1.2. The absolute molecular weight determined by MALLS was 140,000.

EXAMPLE 2

<Tetrafunctional-pinacol-MMA>

Tetrafunctional acrylate (i.e., pentaerythritol tetraacrylate, 1 g, tradename: M-450, manufactured by Toagosei Co., Ltd.) was introduced into a two-necked flask, the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 7.4 ml of a solution of 4,4,5,5-tetramethyl-1,3,2-dioxaborolane (Pinacolborane) at the concentration of 1.0 mol/l in tetrahydrofuran (manufactured by Aldrich) was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

$^1$H-NMR: 5.2 ppm (CH2-B); $^{13}$C-NMR: 29 ppm (CH2-B)

A C—C double bond (C=C) observed in pentaerythritol tetraacrylate at 128 ppm in $^{13}$C-NMR and B—H bond (B—H) observed in 4,4,5,5-tetramethyl-1,3,2-dioxaborolane (Pinacolborane) at 4.8 ppm in $^1$H-NMR were not substantially observed. On the basis of these results, it was confirmed that a polymerization initiator in which 4,4,5,5-tetrametramethyl-1,3,2-dioxaborolane (Pinacolborane) had been added to a carbon-carbon double bond of pentaerythritol tetraacrylate was obtained. Thus, a precursor of the polyfunctional radical polymer of the present invention was obtained.

Subsequently, 1.14 g of methyl methacrylate as an unsaturated hydrocarbon compound was added to 0.5 g of the precursor in a two-necked flask using a syringe. Oxygen (5 ml) was injected thereinto using a gas-tight syringe at 23° C., so as to activate the polymerization initiator. Thus, the polyfunctional radical polymerization initiator according to the present invention serving as a dormant species was synthesized.

Subsequently, 20 g of toluene was added to 20.4 g of methyl methacrylate as an unsaturated hydrocarbon compound, and polymerization was carried out at 60° C. for 4 hours while introducing nitrogen gas. Thus, the polymer was obtained. The yield was 42.3%, the number average molecular weight of the polymer determined by GPC was 14,000, and the molecular weight distribution (weight average molecular weight/number average molecular weight (Mw/Mn)) was 1.1. The absolute molecular weight determined by MALLS was 39,000.

EXAMPLE 3

<Pentafunctional-pinacol-MMA>

Pentafunctional acrylate (i.e., dipentaerythritol pentapolyacrylate, 1 g, tradename: A9550, manufactured by Shin-Nakamura Chemical Co., Ltd.) was introduced into a two-necked flask, the rubber septum was mounted on one neck of the two-necked flask, and a three-way cock with nitrogen balloon was mounted on the other neck With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 7.4 ml of a solution of 4,4,5,5-tetramethyl-1,3,2-dioxaborolane (Pinacolborane) at the concentration of 1.0 mol/l in tetrahydrofuran (manufactured by Aldrich) was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

$^1$H-NMR: 5.2 ppm (CH2-B); $^{13}$C-NMR: 29 ppm (CH2-B)

A C—C double bond (C=C) observed in dipentaerythritol pentaacrylate at 128 ppm in $^{13}$C-NMR and B—H bond (B—H) observed in 4,4,5,5-tetramethyl-1,3,2-dioxaborolane (Pinacolborane) at 4.8 ppm in $^1$H-NMR were not substantially observed. On the basis of these results, it was confirmed that a polymerization initiator in which 4,4,5,5-tetramethyl-1,3,2-dioxaborolane (Pinacolborane) had been added to a carbon-carbon double bond of dipentaerythritol penta-polyacrylate was obtained. Thus, a precursor of the polyfunctional radical polymer of the present invention was obtained.

Subsequently, 0.95 g of methyl methacrylate as an unsaturated hydrocarbon compound was added relative to 0.5 g of the precursor into a two-necked flask using a syringe. Oxygen (5 ml) was injected thereinto using a gas-tight syringe at 23° C., so as to activate the polymerization initiator. Thus, the polyfunctional radical polymerization initiator according to the present invention serving as a dormant species was synthesized.

Subsequently, 20 g of toluene was added to 16.5 g of methyl methacrylate as an unsaturated hydrocarbon compound, and polymerization was carried out in a nitrogen gas atmosphere for 1 hour. Thus, the polymer was obtained. The yield was 42.3%, the number average molecular weight of the polymer determined by GPC was 4,000, and the molecular weight distribution (weight average molecular weight/number average molecular weight (Mw/Mn)) was 1.1. The absolute molecular weight determined by MALLS was 13,900.

EXAMPLE 4

<Trifunctional-pinacol-St>

Trifunctional acrylate (i.e., tris(2-acryloyloxyethyl)isocyanurate, 1 g, manufactured by Hitachi Chemical Company, Ltd.) was introduced into a two-necked flask, the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 7.4 ml of a solution of 4,4,5,5-tetramethyl-1,3,2-dioxaborolane (Pinacolborane) at the concentration of 1.0 mol/l in tetrahydrofuran (manufactured by Aldrich) was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

$^1$H-NMR: 5.2 ppm (CH2-B); $^{13}$C-NMR: 29 ppm (CH2-B)

A C—C double bond (C=C) observed in tris(2-acryloyloxyethyl)isocyanurate at 128 ppm in $^{13}$C-NMR and B—H bond (B—H) observed in 4,4,5,5-tetramethyl-1,3,2-dioxaborolane (Pinacolborane) at 4.8 ppm in $^1$H-NMR were not substantially observed. On the basis of these results, it was confirmed that a polymerization initiator in which 4,4,5,5-tetramethyl-1,3,2-dioxaborolane (Pinacolborane) had been added to a carbon-carbon double bond of tris(2-acryloyloxyethyl)isocyanurate was obtained.

Subsequently, 0.74 g of methyl methacrylate as an unsaturated hydrocarbon compound was added relative to 0.5 g of the precursor into a two-necked flask using a syringe. Oxygen (5 ml) was injected thereinto using a gas-tight syringe at 23° C., so as to activate the polymerization initiator. Thus, the polyfunctional radical polymerization initiator according to the present invention serving as a dormant species was synthesized.

Toluene (20 g) was added to 19.3 g of styrene as an unsaturated hydrocarbon compound, polymerization was carried out in a nitrogen gas atmosphere at 60° C. for 5 hours, and a polymerization solution was subjected to reprecipitation using methanol (Wako Pure Chemical Co.). Thus, the polymer was obtained. The yield was 42.3%, the number average molecular weight of the polymer determined by GPC was 76,000 and the molecular weight distribution (weight average molecular weight/number average molecular weight (Mw/Mn)) was 1.1. The absolute molecular weight determined by MALLS was 250,000.

(Synthesis of Multi-branched Polymer Via Method of Synthesis 2)

EXAMPLE 5

1-Phenyl-3-buten-1-ol (1 g, manufactured by Tokyo Chemical Industry Co., Ltd.) was introduced into a two-necked, eggplant-type flask (hereafter, referred to as a "two-necked flask"), the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve 1-phenyl-3-buten-1-ol in the solvent. Thereafter, 0.61 g of dimethoxyboronic acid was introduced into the two-necked flask using a syringe, and the reaction was allowed to proceed at room temperature for 12 hours with agitation. After the completion of the reaction, tetrahydrofuran was removed by vacuum distillation using a diaphragm pump. Thus, a boronate ester compound having a double bond was obtained.

The obtained boronate ester compound (1.0 g) and 0.57 g of trifunctional acrylate (i.e., tris(2-acryloyloxyethyl)isocyanurate, manufactured by Hitachi Chemical Company, Ltd.) were subjected to the reaction in a nitrogen atmosphere with the use of 5 ml of tetrahydrofuran as a solvent and 1 mg of 2,2-azobisisobutyronitrile as a radical polymerization initiator at 60° C. for 3 hours. After the completion of the reaction, tetrahydrofuran was removed by vacuum distillation using a diaphragm pump to obtain a reaction product. Thus, the polyfunctional radical polymerization initiator according to the present invention was obtained.

Toluene (20 g) was added to 17.0 g of styrene as an unsaturated hydrocarbon compound, 0.5 g of the polyfunctional radical polymerization initiator obtained above was added as a solid content, the polymerization initiator was activated at 23° C. in an oxygen atmosphere, polymerization was carried out at 60° C. for 5 hours while introducing nitrogen gas, and a polymerization solution was subjected to reprecipitation using methanol (Wako Pure Chemical Co.). Thus, the polymer was obtained. The yield was 40.1%, the number average molecular weight of the polymer determined by GPC was 13,000, and the molecular weight distribution (weight average molecular weight/number average molecular weight (Mw/Mn)) was 1.2. The absolute molecular weight determined by MALLS was 41,000.

EXAMPLE 6

1-Phenyl-3-buten-1-ol (1 g, manufactured by Tokyo Chemical Industry Co., Ltd.) was introduced into a two-necked, eggplant-type flask (hereafter, referred to as a "two-necked flask"), the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve 1-phenyl-3-buten-1-ol in the solvent. Thereafter, 0.61 g of dimethoxyboronic acid was introduced into the two-necked flask using a syringe, and the reaction was allowed to proceed at room temperature for 12 hours with agitation. After the completion of the reaction, tetrahydrofuran was removed by vacuum distillation using a diaphragm pump. Thus, a boronate ester compound having a double bond was obtained.

The obtained boronate ester compound (1.0 g) and 0.37 g of tetrafunctional acrylate (i.e., pentaerythritol tetraacrylate; tradename: M-450, manufactured by Toagosei Co., Ltd.) were subjected to the reaction in a nitrogen atmosphere with the use of 5 ml of tetrahydrofuran as a solvent and 1 mg of 2,2-azobisisobutyronitrile as a radical polymerization initiator at 60° C. for 3 hours. After the completion of the reaction, tetrahydrofuran was removed by vacuum distillation using a diaphragm pump to obtain a reaction product. Thus, the polyfunctional radical polymerization initiator according to the present invention was obtained.

Toluene (20 g) was added to 17.0 g of styrene as an unsaturated hydrocarbon compound, 0.5 g of the polymerization initiator obtained above was added as a solid content, the polymerization initiator was activated at 23° C. in an oxygen atmosphere, and polymerization was carried out at 60° C. for 4 hours while introducing nitrogen gas. Thus, the polymer was obtained. The yield was 42.3%, the number average molecular weight of the polymer determined by GPC was 14,000, and the molecular weight distribution (weight average molecular weight-number average molecular weight (Mw/Mn)) was 1.1. The absolute molecular weight determined by MALLS was 39,000.

Examples 1 to 6 demonstrate that the polyfunctional polymerization initiator according to the present invention can be synthesized and that a multi-branched polymer can be synthesized via polymerization with the use of the polyfunctional polymerization initiator according to the present invention.

COMPARATIVE EXAMPLE 1

Trifunctional acrylate (i.e., tris(2-acryloyloxyethyl)isocyanurate, 1 g, manufactured by Hitachi Chemical Company, Ltd.) was introduced into a two-necked flask, the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 14.7 ml of a solution of 9-borabicyclo[3,3,1]nonane at the concentration of 0.5 mol/l in tetrahydrofuran was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

$^1$H-NMR: 5.2 ppm (CH2-B); $^{13}$C-NMR: 29 ppm (CH2-B)

A C—C double bond (C=C) observed in tris(2-acryloyloxyethyl)isocyanurate at 128 ppm in $^{13}$C-NMR and B—H bond (B—H) observed in 9-borabicyclo[3,3,1]nonane at 4.8 ppm in $^1$H-NMR were not substantially observed. On the basis of these results, it was confirmed that a polymerization initiator in which 9-borabicyclo[3,3,1]nonane had been added to the carbon-carbon double bond of tris(2-acryloyloxyethyl)isocyanurate was obtained. Subsequently, 20 g of toluene was added to 19.0 g of methyl methacrylate as an unsaturated hydrocarbon compound, 0.5 g of the polymerization initiator obtained above was added as a solid content, the polymerization initiator was activated at 23° C. in an oxygen atmosphere, and polymerization was carried out at 60° C. for 5 hours while introducing nitrogen gas. Thus, the polymer was obtained. The yield was 51.2%, the weight average molecular weight of the polymer determined by GPC was 14,000, and the molecular weight distribution (weight average molecular weight/number average molecular weight (Mw/Mn)) was 2.7.

COMPARATIVE EXAMPLE 2

Tetrafunctional acrylate (i.e., pentaerythritol tetraacrylate, 1 g, tradename: M-450, manufactured by Toagosei Co., Ltd.) was introduced into a two-necked flask, the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 20.1 ml of a solution of 9-borabicyclo[3,3,1]nonane at 0.5 mol/l in tetrahydrofuran was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

$^1$H-NMR: 5.2 ppm (CH2-B); $^{13}$C-NMR: 29 ppm (CH2-B)

A C—C double bond (C=C) observed in pentaerythritol tetraacrylate at 128 ppm in $^{13}$C-NMR and B—H bond (B—H) observed in 9-borabicyclo[3,3,1]nonane at 4.8 ppm in $^1$H-NMR were not substantially observed. On the basis of these results, it was confirmed that a polymerization initiator in which 9-borabicyclo[3,3,1]nonane had been added to the carbon-carbon double bond of pentaerythritol tetraacrylate was obtained. Subsequently, 20 g of toluene was added to 20.9 g of methyl methacrylate as an unsaturated hydrocarbon compound, 0.5 g of the polymerization initiator obtained above was added as a solid content, the polymerization initiator was activated at 23° C. in an oxygen atmosphere, and polymerization was carried out at 60° C. for 5 hours while introducing nitrogen gas. Thus, the polymer was obtained. The yield was 52.3%, the weight average molecular weight of the polymer determined by GPC was 16,000, and the molecular weight distribution (weight average molecular weight/number average molecular weight (Mw/Mn)) was 2.8.

COMPARATIVE EXAMPLE 3

Pentafunctional acrylate (i.e., dipentaerythritol pentapolyacrylate, 1 g, tradename: A9550, manufactured by Shin-Nakamura Chemical Co., Ltd.) was introduced into a two-necked flask, the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 21.1 ml of a solution of 9-borabicyclo[3,3,1]nonane at the concentration of 0.5 mol in tetrahydrofuran was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

1H-NMR: 5.2 ppm (CH2-B); $^{13}$C-NMR: 29 ppm (CH2-B)

A C—C double bond (C=C) observed in pentaerythritol tetraacrylate at 128 ppm in $^{13}$C-NMR and B—H bond (B—H) observed in 9-borabicyclo[3,3,1]nonane at 4.8 ppm in $^{1}$H-NMR were not substantially observed. On the basis of these results, it was confirmed that a polymerization initiator in which 9-borabicyclo[3,3,1]nonane had been added to the carbon-carbon double bond of pentaerythritol tetraacrylate was obtained. Subsequently, 20 g of toluene was added to 16.7 g of methyl methacrylate as an unsaturated hydrocarbon compound, 0.5 g of the polymerization initiator obtained above was added as a solid content, the polymerization initiator was activated at 23° C. in an oxygen atmosphere, and polymerization was carried out at 60° C. for 5 hours while introducing nitrogen gas. Thus, the polymer was obtained. The yield was 51.9%, the weight average molecular weight of the polymer determined by GPC was 15,000, and the molecular weight distribution (weight average molecular weight/number average molecular weight (Mw/Mn)) was 2.6.

COMPARATIVE EXAMPLE 4

Trifunctional acrylate (i.e., tris(2-acryloyloxyethyl)isocyanurate, 1 g, manufacture by Hitachi Chemical Company, Ltd.) was introduced into a two-necked flask, the rubber septum was mounted on one neck of the two-necked flask, and a three-way cock with nitrogen balloon was mounted on the other neck. With the use of the mounted three-way cock with nitrogen balloon, the atmosphere in the two-necked flask was converted into a nitrogen atmosphere. As a solvent, 20 ml of tetrahydrofuran was injected into the flask using a syringe, and the flask was agitated at room temperature, so as to dissolve tris(2-acryloyloxyethyl)isocyanurate in the solvent. Thereafter, 14.7 ml of a solution of 9-borabicyclo[3,3,1]nonane at the concentration of 0.5 mol/l in tetrahydrofuran was injected into the flask using a syringe, and the reaction was allowed to proceed in a nitrogen atmosphere at 23° C. for 6 hours. After the completion of the reaction, tetrahydrofuran was removed by vacuum distillation using a diaphragm pump. The results of nuclear magnetic resonance spectral measurements of the products are shown below.

1H-NMR: 5.2 ppm (CH2-B); $^{13}$C-NMR: 29 ppm (CH2-B)

A C—C double bond (C=C) observed in tris(2-acryloyloxyethyl)isocyanurate at 128 ppm in $^{13}$C-NMR and B—H bond (B—H) observed in 9-borabicyclo[3,3,1]nonane at 4.8 ppm in $^{1}$H-NMR were not substantially observed. On the basis of these results, it was confirmed that a polymerization initiator in which 9-borabicyclo[3,3,1]nonane had been added to the carbon-carbon double bond of tris(2-acryloyloxyethyl)isocyanurate was obtained. Subsequently, 20 g of toluene was added to 19.8 g of styrene as an unsaturated hydrocarbon compound, 0.5 g of the polymerization initiator obtained above was added as a solid content, the polymerization initiator was activated at 23° C. in an oxygen atmosphere, and polymerization was carried out at 60° C. for 5 hours while introducing nitrogen gas. Thus, the polymer was obtained. The yield was 48.3%, the weight average molecular weight of the polymer determined by GPC was 16,000, and the molecular weight distribution (weight average molecular weight/number average molecular weight (Mw/Mn)) was 2.9.

In Comparative Examples 1 to 4, the multi-branched polymer, which was synthesized with the use of the polyfunctional polymerization initiator of the alkylborane compound having no alkoxy or phenyl group, shows a broad range of molecular weight distribution. Thus, it was indicated that such polymer may include branch defects and unnecessary molecular chains.

EXAMPLE 7

Polymer "a" (5 g, the polymer obtained in Example 1) was dissolved in 5 ml of toluene to prepare a varnish, and viscosity thereof was measured. Polymer "a" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "a" and a toluene solution was 3,300 mPa·s.

EXAMPLE 8

Polymer "c" (5 g, the polymer obtained in Example 3) was dissolved in 5 ml of toluene to prepare a varnish, and viscosity thereof was measured. Polymer "c" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "c" and a toluene solution was 700 mPa·s.

EXAMPLE 9

Polymer "d" (5 g, the polymer obtained in Example 4) was dissolved in 5 ml of toluene to prepare a varnish, and viscosity thereof was measured. Polymer "d" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "d" and a toluene solution was 3,900 mPa·s.

EXAMPLE 10

Polymer "e" (5 g, the polymer obtained in Example 5) was dissolved in 5 ml of toluene to prepare a varnish, and viscosity thereof was measured. Polymer "e" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "e" and a toluene solution was 1,500 mPa·s.

COMPARATIVE EXAMPLE 5

Polymer "g" (5 g, the polymer obtained in Comparative Example 1) was dissolved in 5 ml of toluene to prepare a varnish, and viscosity thereof was measured. Polymer "g" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "g" and a toluene solution was 5,000 mPa·s.

COMPARATIVE EXAMPLE 6

Polymer "h" (5 g, the polymer obtained in Comparative Example 2) was dissolved in 5 ml of toluene to prepare a varnish, and viscosity thereof was measured. Polymer "h" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "h" and a toluene solution was 5,300 mPa·s.

COMPARATIVE EXAMPLE 7

Polymer "i" (5 g, the polymer obtained in Comparative Example 3) was dissolved in 5 ml of toluene to prepare a varnish, and viscosity thereof was measured. Polymer "i" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "i" and a toluene solution was 6,300 mPa·s.

COMPARATIVE EXAMPLE 8

Polymer "j" (5 g, the polymer obtained in Comparative Example 4) was dissolved in 5 ml of toluene to prepare a varnish, and viscosity thereof was measured. Polymer "j" and toluene were introduced into a 10-ml screw cap tube, and the tube was tightly closed with a cap. The content in the screw cap tube was agitated with the use of Mix rotor VMR-5 (manufactured by AS ONE). It was confirmed 30 minutes later that a solid component of the polymer had disappeared from the screw cap tube, and the resultant was designated as the varnish. Viscosity of the varnish composed of Polymer "j" and a toluene solution was 7,200 mPa·s.

Examples 7 to 10 and Comparative Examples 5 to 8 demonstrate that the viscosity of the varnish comprising the multi-branched polymer synthesized with the use of polyfunctional polymerization initiator according to the present invention is lower than that of the varnish comprising the high-molecular-weight compound having the equivalent molecular weight.

In general, a high-molecular-weight compound is used to enhance the strength of adhesive agents and coating materials; however, viscosity of a varnish increases as a molecular weight increases.

The increase in varnish viscosity is disadvantageous in terms of processability. However, the multi-branched polymer according to the present invention can strengthen adhesive agents or coating materials without increasing the varnish viscosity.

TABLE I

| | | Poly functional | | Polymer | | | |
|---|---|---|---|---|---|---|---|
| | Borane compound | Unsaturated compound | Monomer | | Mn | Mw/Mn | Absolute molecular weight |
| Ex. 1 | 4,4,5,5-Tetramethyl-1,3,2-dioxaborolane | Tris(2-acryloyloxyethyl) isocyanurate | Methyl methacrylate | a | 15,000 | 1.2 | 140,000 |
| Ex. 2 | 4,4,5,5-Tetramethyl-1,3,2-dioxaborolane | Pentaerythritol tetraacrylate | Methyl methacrylate | b | 14,000 | 1.1 | 39,000 |
| Ex. 3 | 4,4,5,5-Tetramethyl-1,3,2-dioxaborolane | Dipentaerythritol tetraactylate | Methyl methacrylate | c | 4,000 | 1.1 | 13,900 |
| Ex. 4 | 4,4,5,5-Tetramethyl-1,3,2-dioxaborolane | Tris(2-acryloyloxyethyl) isocyanurate | Styrene | d | 76,000 | 1.1 | 250,000 |
| Ex. 5 | Dimethoxyboronic acid | Tris(2-acryloyloxyethyl) isocyanurate | Styrene | e | 13,000 | 1.2 | 41,000 |

TABLE I-continued

| | Borane compound | Poly functional Unsaturated compound | Monomer | | Polymer Mn | Mw/Mn | Absolute molecular weight |
|---|---|---|---|---|---|---|---|
| Ex. 6 | Dimethoxyboronic acid | Pentaerythritol tetraacrylate | Styrene | f | 14,000 | 1.1 | 39,000 |
| Comp. Ex. 1 | 9-Borabicyclo[3,3,1] nonane | Tris(2-acryloyloxyethyl) isocyanurate | Methyl methacrylate | g | 14,000 | 2.7 | — |
| Comp. Ex. 2 | 9-Borabicyclo[3,3,1] nonane | Pentaerythritol tetraacrylate | Methyl methacrylate | h | 16,000 | 2.8 | — |
| Comp. Ex. 3 | 9-Borabicyclo[3,3,1] nonane | Dipentaerythritol tetraacrylate | Methyl methacrylate | i | 15,000 | 2.6 | — |
| Comp. Ex. 4 | 9-Borabicyclo[3,3,1] nonane | Tris(2-acryloyloxyethyl) isocyanurate | Styrene | j | 14,000 | 2.9 | — |

TABLE 2

| | Polymer | Viscosity (mPa · s) |
|---|---|---|
| Ex. 7 | a | 3,300 |
| Ex. 8 | c | 700 |
| Ex. 9 | d | 3,900 |
| Ex. 10 | e | 1,500 |
| Comp. Ex. 5 | g | 5,000 |
| Comp. Ex. 6 | h | 5,300 |
| Comp. Ex. 7 | i | 6,300 |
| Comp. Ex. 8 | j | 7,200 |

DESCRIPTION OF NUMERICAL REFERENCES

1: Lead frame; 2: mold sealant; 3: semiconductor device; 4: bonding wire; 200: DIP

The invention claimed is:

1. A polyfunctional radical polymerization initiator represented by Formula 1:

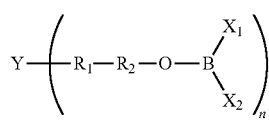

Formula 1 wherein n is an integer of 1 or larger; Y is a polyfunctional unsaturated compound residue; $R_1$ is a hydrocarbon group; $R_2$ is a structure in which one molecule of a radically polymerizable unsaturated hydrocarbon compound is bound to $R_1$ and the oxygen atom; $X_1$ of B—$X_1$ (boron-$X_1$) bond is an alkoxy or phenyl group; and $X_2$ of B—$X_2$ (boron-$X_2$) bond is an alkoxy or phenyl group, wherein the polyfunctional unsaturated compound residue has a branched or cyclic molecular structure and comprises at least one of hydrocarbon, nitrogen, silicon, and phosphorus.

2. The polyfunctional radical polymerization initiator according to claim 1, wherein the structure of $R_2$ is, as an unsaturated hydrocarbon compound residue before it is positioned between $R_1$ and the oxygen atom, selected from the group consisting of an aromatic vinyl compound, an aromatic allyl compound, a heterocycle-containing vinyl compound, a heterocycle-containing an allyl compound, an alkyl (meth)acrylate, an unsaturated monocarboxylic acid ester, a fluoroalkyl (meth)acrylate, a siloxanyl compound, a mono(meth)acrylate and di(meth)acrylate of an alkylene glycol, an alkoxyalkyl (meth)acrylate, a cyanoalkyl (meth) acrylate, acrylonitrile, and methacrylonitrile.

3. The polyfunctional radical polymerization initiator according to claim 1, wherein the structure of $R_2$ is, as an unsaturated hydrocarbon compound residue before it is positioned between $R_1$ and the oxygen atom, selected from the group consisting of an oligo(meth)acrylate of a polyhydric alcohol, a hydroxyalkyl (meth)acrylate, a hydroxyalkylester of an unsaturated carboxylic acid, an unsaturated alcohol, an unsaturated (mono)carboxylic acid, an unsaturated polycarboxylic acid, an unsaturated polycarboxylic anhydrate, a monoester and diester of an unsaturated polycarboxylic acid or unsaturated polycarboxylic anhydrate, an epoxy-group-containing unsaturated compound, a diene compound, vinyl chloride, vinyl acetate, sodium isoprene sulfonate, a cinnamic acid ester, a crotonic acid ester, dicyclopentadienyl, and ethylidene norbornene.

4. The polyfunctional radical polymerization initiator according to claim 1, wherein the polyfunctional unsaturated compound residue has a structure having one atom as a center skeleton and at least two unsaturated hydrocarbon groups bound to the atom.

5. A polyfunctional radical polymerization initiator represented by Formula 1:

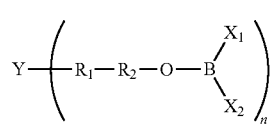

Formula 1 wherein n is an integer of 1 or larger; Y is a polyfunctional unsaturated compound residue; $R_1$ is a hydrocarbon group; $R_2$ is a structure in which one molecule of a radically polymerizable unsaturated hydrocarbon compound is bound to $R_1$ and the oxygen atom; $X_1$ of B—$X_1$ (boron-$X_1$) bond is an alkoxy or phenyl group; and $X_2$ of B—$X_2$ (boron-$X_2$) bond is an alkoxy or phenyl group, wherein the polyfunctional unsaturated compound residue has a molecular structure selected from the group consisting of ester bond, urethane bond, amide bond, thioester bond, siloxane bond, carbonyl group, carboxyl group, amino group, alkylamino group, and dialkylamino group.

6. A polyfunctional radical polymerization initiator represented by Formula 1:

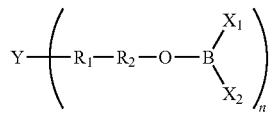

Formula 1 wherein n is an integer of 1 or larger; Y is a polyfunctional unsaturated compound residue; $R_1$ is a hydrocarbon group; $R_2$ is a structure in which one molecule of a radically polymerizable unsaturated hydrocarbon compound is bound to $R_1$ and the oxygen atom; $X_1$ of B—$X_1$ (boron-$X_1$) bond is an alkoxy or phenyl group; and $X_2$ of B—$X_2$, (boron-$X_2$) bond is an alkoxy or phenyl group, wherein the polyfunctional unsaturated compound residue has a molecular structure selected from the group consisting of pyridyl group, pyrrolidyl group, isocyanuric acid ester skeleton, cyanuric acid ester skeleton, hexahydrotriazine skeleton, maleimide skeleton, imidazole skeleton, and organic silicon skeleton.

7. The polyfunctional radical polymerization initiator according to claim 1, wherein $R_1$—$R_2$ bond is alkyl bond.

8. A multi-branched polymer prepared through polymerization with the use of the polymerization initiator according to claim 7.

9. The polyfunctional radical polymerization initiator according to claim 5, wherein $R_1$—$R_2$ bond is alkyl bond.

10. A multi-branched polymer prepared through polymerization with the use of the polymerization initiator according to claim 9.

11. The polyfunctional radical polymerization initiator according to claim 6, wherein $R_1$—$R_2$ bond is alkyl bond.

12. A multi-branched polymer prepared through polymerization with the use of the polymerization initiator according to claim 11.

* * * * *